United States Patent [19]

Hughes

[11] 4,372,169
[45] Feb. 8, 1983

[54] VORTEX GENERATING MASS FLOWMETER

[75] Inventor: Nathaniel Hughes, Palm Springs, Calif.

[73] Assignee: Vortech Sciences, Inc., Palm Springs, Calif.

[21] Appl. No.: 109,839

[22] Filed: Jan. 7, 1980

Related U.S. Application Data

[63] Continuation-in-part of Ser. No. 40,557, May 21, 1979, Pat. No. 4,240,293, which is a continuation-in-part of Ser. No. 886,289, Mar. 13, 1978, Pat. No. 4,189,101, and Ser. No. 886,288, Mar. 13, 1978, Pat. No. 4,192,465, each is a continuation-in-part of Ser. No. 785,838, Apr. 8, 1977, Pat. No. 4,109,862.

[51] Int. Cl.³ .......................... G01F 1/32; G01F 1/34
[52] U.S. Cl. ............................ 73/861.52; 73/861.22
[58] Field of Search .......... 73/861.22, 861.52, 861.63, 73/861.64

[56] References Cited

U.S. PATENT DOCUMENTS

| 790,888 | 5/1905 | Ferris | 73/861.64 |
| 1,126,275 | 1/1915 | Rice | 73/861.64 |
| 1,143,631 | 6/1915 | Keller | 73/861.63 |
| 2,146,371 | 2/1939 | Dunglinson | 73/861.64 |
| 2,197,214 | 4/1940 | Hollander | 73/861.64 |
| 2,240,119 | 4/1941 | Montgomery et al. | 73/861.63 |
| 3,874,234 | 4/1975 | Burgess | 73/861.22 |

FOREIGN PATENT DOCUMENTS

| 405084 | 10/1924 | Fed. Rep. of Germany | 73/861.23 |
| 2357868 | 2/1978 | France | 73/861.24 |
| 764889 | 1/1957 | United Kingdom | 73/861.23 |

*Primary Examiner*—Herbert Goldstein
*Attorney, Agent, or Firm*—Christie, Parker & Hale

[57] ABSTRACT

Drag is produced in a gas stream by a bluff body (47), and is converted to low pressure stable and continuous vortices by a restriction (56). The difference in gas pressure is sensed (14) between a point (15) outside the flow passage in communication therewith and a point (16) inside the flow passage between the restriction and the bluff body. The resultant flowmeter may be connected in line or as a bypass in a gas system.

16 Claims, 11 Drawing Figures

VORTEX GENERATING MASS FLOWMETER

CROSS REFERENCE TO RELATED APPLICATIONS

This is a continuation-in-part of application Ser. No. 40,557, filed May 21, 1979, now U.S. Pat. No. 4,240,293, which is a continuation-in-part of application Ser. No. 886,289, filed on Mar. 13, 1978, now U.S. Pat. Nos. 4,189,101 and 4,192,465, respectively, the disclosures of which are incorporated fully herein by reference, which are continuations-in-part of Ser. No. 785,838, filed Apr. 8, 1977, now U.S. Pat. No. 4,109,862.

BACKGROUND OF THE INVENTION

This invention relates to gas flow rate measurement and, more particularly, to a vortex generating mass flowmeter usable over a wide range of flow rates.

There are many different types of flowmeters in use today. One type, which is known as a vortex shedding flowmeter, generates intermittent, unstable vortices with a transversely elongated bluff body positioned in the flow stream passing through an unrestricted fluid line. The frequency of the intermittent vortices or perturbations is a measure of the flow rate through the fluid line, and this frequency is sensed to provide a flow rate reading. The devices are generally limited to liquid flow rate measurement due to the effect of compressibility of the gas on the vortex shedding process. A typical vortex shedding flowmeter is disclosed in Rodely U.S. Pat. No. 3,572,117, issued Mar. 23, 1971.

Another type of flowmeter measures the pressure difference across a calibrated orifice plate. In the case of gas measurement, due to compressibility effects, the mass flow rate is not only dependent upon the pressure difference but also temperature and density variations, and the relationship is nonlinear and highly complex. Thus, the measured pressure difference must be processed further to give a true reading of mass flow rate. These devices generally read gas flow over a limited range due to rapidly increasing pressure difference across the device.

SUMMARY OF THE INVENTION

According to the invention, controlled drag is produced in a gas stream passing through a flow passage, and the drag is converted completely and efficiently to subambient pressure, through the mechanism of stable and continuous vortices. The vortex pressure referenced to the ambient of the device is then a measure of the mass flow rate. Specifically, the vortex generating flowmeter has a flow passage between an inlet and an outlet, a restriction formed in the flow passage, and a bluff body forming an annulus in the flow passage. The difference in gas pressure is sensed between a point outside the flow passage in communication therewith and a point inside the flow passage between the restriction and the bluff body. This pressure difference is a direct and totally repeatable measure of the gas mass flow rate through the flow passage irrespective of compressibility effects. The combination of the restriction and the bluff body produces highly stable vortices, which provide a predictable relationship between gas flow rate and the sensed pressure difference. Specifically, the bluff body generates the vortices and the annulus and restriction confine and focus the vortices to follow a continuous stable path rotating about the axis.

BRIEF DESCRIPTION OF THE DRAWINGS

The features of specific embodiments of the best mode contemplated of carrying out the invention are illustrated in the drawings, in which.

DETAILED DESCRIPTION OF THE SPECIFIC EMBODIMENT

Figure 1:
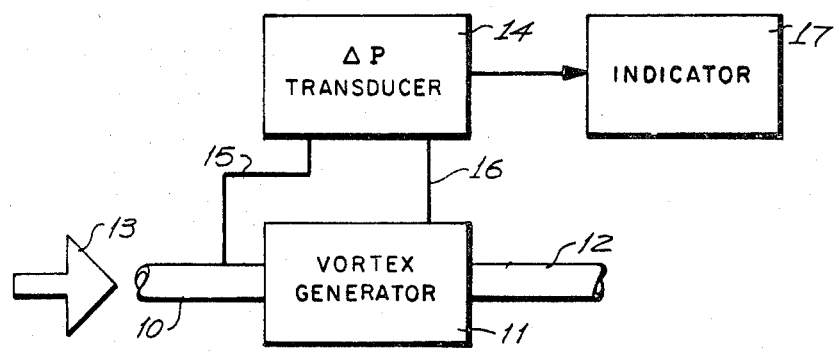
FIG. 1 is a schematic diagram of a flowmeter incorporating the principles of the invention that is connected in line in a gas system.

In FIG. 1, a gas system has a section 10 of gas line connected to the inlet of a vortex generator 11 and a section 12 of gas line connected to the outlet of vortex generator 11. Thus, vortex generator 11 is connected in line in the gas system, i.e., all the fluid flowing through sections 10 and 12 passes through vortex generator 11. An arrow 13 designates the direction of fluid flow through the system, i.e., from left to right as viewed in FIG. 1. A differential pressure ($\Delta P$) transducer 14 has an input conduit 15 that taps into the gas system in section 10 and an input conduit 16 that taps into vortex generator 11. (Alternatively, input conduit 15 could tap into conduit 12.) Transducer 14 produces an electrical output signal related to the pressure difference between the points tapped into by input conduits 15 and 16. The output signal produced by transducer 14 is displayed on an indicator 17 in digital or analog form.

Figure 2:
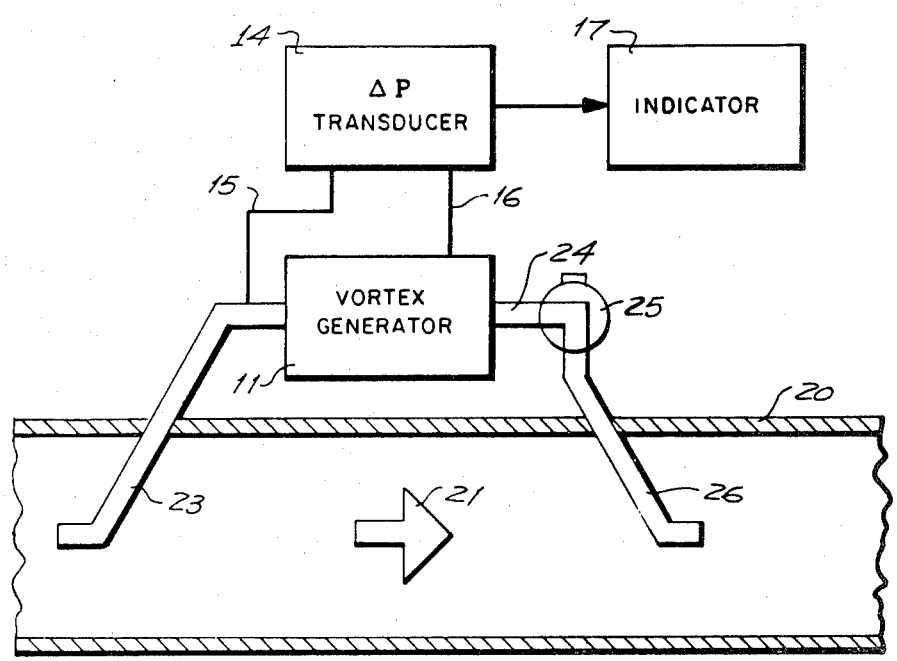
FIG. 2 is a schematic diagram of a flowmeter incorporating the principles of the invention that is connected as a bypass in a gas system.

In FIG. 2, gas flows through a gas line 20 of a gas system in the direction of an arrow 21, i.e., from left to right. Vortex generator 11 is physically located outside line 20. A sampling conduit 23, which has an open end facing toward the gas flowing in line 20, is connected to the inlet of vortex generator 11. The outlet of vortex generator 11 is connected by a conduit 24 to a first port of a two port, 2-way valve 25 physically located outside line 20. A sampling conduit 26, which has an open end facing away from the flowing gas in line 20, is connected to a second port of valve 25. The third port of valve 25 is vented to the atmosphere. In one position of valve 25, a sample of the gas flowing through line 20 is coupled by conduit 23 through vortex generator 11 and conduit 26 back into line 20. In the other position of valve 25, a sample of the gas is coupled by conduit 23 through vortex generator 11 and is vented to the atmosphere. Valve 25 could be replaced by a permanent connection providing one of the described flow paths or the other for the sample gas. Thus, vortex generator 11 is connected to bypass line 20 in the gas system and to measure a sample of the gas that is a fixed percentage of the total gas flow through line 20. Usually, a sample of less than 5% is taken in a bypass arrangement. Input conduit 15 of ΔP transducer 14 taps into sample conduit 23, and input conduit 16 taps into vortex generator 11 to produce an electrical signal related to the pressure difference at the tap-in points, which is a measure of the flow rate of all the gas flowing through line 20. (Alternatively, input conduit 15 could tap into line 20 or sample conduit 26.)

By way of example, ΔP transducer 14 could be of the conventional bellows or diaphragm type, wherein displacement of the bellows or diaphragm is indicative of the pressure difference, and a strain gage or other displacement sensing device produces the electrical signal. The electrical signal produced by transducer 14 could also be used in a process controller, or the pressure difference could be directly used to actuate a process control mechanism, such as a control valve or pump.

Vortex generator 11 has a flow passage in which a restriction is formed, and one or more bluff bodies forming an annulus are located. By way of example, any of the devices having a bluff body described in my following patent and patent applications, the disclosures of which are incorporated fully herein by reference, could be employed as vortex generator 11: U.S. Pat. No. 4,109,862, issued on Aug. 29, 1978; application Ser. No. 886,289, filed on Mar. 13, 1978; and application Ser. No. 951,621, filed on Oct. 16, 1978.

Figure 3:
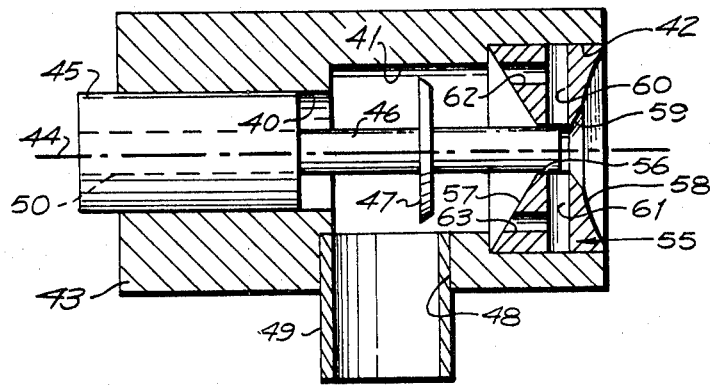
FIG. 3 is a side sectional view of one embodiment of a flowmeter incorporating the principles of the invention.

In FIG. 3, a preferred embodiment of vortex generator 11 is shown. A cylindrical bore 40, a cylindrical counterbore 41, and a large cylindrical counterbore 42 extend through a body member 43 from end to end in alignment with an axis 44. A cylindrical plug 45 fits in bore 40. A hollow rod 46, part of which fits in a bore 50 through plug 45, extends from one end of plug 45 completely through counterbore 41 and into counterbore 42 in alignment with axis 44. Rod 46 is secured to plug 45 by a force fit, welding, or the like. Once the position of plug 45 is set, it is fixed within bore 40 by a set screw, welding, or the like, so rod 46 cannot move. A truncated frustum 47 is fixedly mounted on rod 46 within counterbore 41 in alignment with axis 44. The base of frustum 47 faces toward bore 40. An annulus is formed between the edge of frustum 47 and the surface of counterbore 41. A bore 48 is formed in body member 43 in alignment with an inlet axis perpendicular to axis 44 so as to open into counterbore 41. A cylindrical inlet pipe section 49 fits into bore 48. A cylindrical insert 55 fits in counterbore 42. Insert 55 has in alignment with axis 44 a cylindrical bore 56, a concave conical surface 57 on the side of bore 56 opening toward rod 46, and a concave semispherical outlet surface 58 on the side of bore 56 opening away from rod 46. Bore 56 is larger in diameter than rod 46, which extends partially therein. Surface 58 forms a fluid outlet. A shallow concave conical surface 59 is formed where surface 58 joins the edge of bore 56. Rod 46 has an open end in bore 56 facing downstream. Radial bores 60 and 61 extend through insert 55 from its periphery to bore 56 into which they open from diametrically opposite directions. In other words, bores 60 and 61 are axially aligned with each other. Bores 62 and 63 extend through insert 55 parallel to axis 44 between surface 57 and bores 60 and 61, respectively. In one embodiment, the components of FIG. 3 would have the dimensions of the device described in connection with FIG. 2 in my application Ser. No. 951,621, except that bore 48 would have the dimensions of the corresponding element in FIG. 1 of my said application.

Pipe section 49 is the inlet of the device, and the opening enclosed by surface 58 is the outlet. Bore 41 and counterbore 42 together comprise a main flow passage from the inlet to the outlet; bore 41 comprises an upstream portion thereof, and counterbore 42 comprises a downstream portion thereof. Axis 44 comprises a flow axis, with which the flow passage is aligned. Bore 56 comprises a restriction in the downstream portion of the main flow passage. Bores 62 and 60 comprise one auxiliary flow passage from the upstream portion of the main flow passage to the restriction, and bores 63 and 61 comprise another auxiliary flow passage to the restriction. Frustum 47 comprises a bluff body. Surface 57 comprises a vortex collection section for coupling the upstream portion of the main flow passage to the restriction, and surface 59 comprises a diverging section coupling the restriction to surface 58.

Input conduit 16 of ΔP transducer 14 is connected to the hollow interior of rod 46, thereby sensing the pressure at the end of rod 46, i.e., at a point between the bluff body, i.e., frustum 47, and the restriction, i.e., bore 56. A stable vortex generation in the described device results in a predictable, repeatable, and continuous relationship between the mass flow rate through the device and the sensed pressure difference. This is the case whether the vortex generator is connected in line in the system as shown in FIG. 1, or connected to bypass the system as shown in FIG. 2, although the relationship is different.

Figure 9:
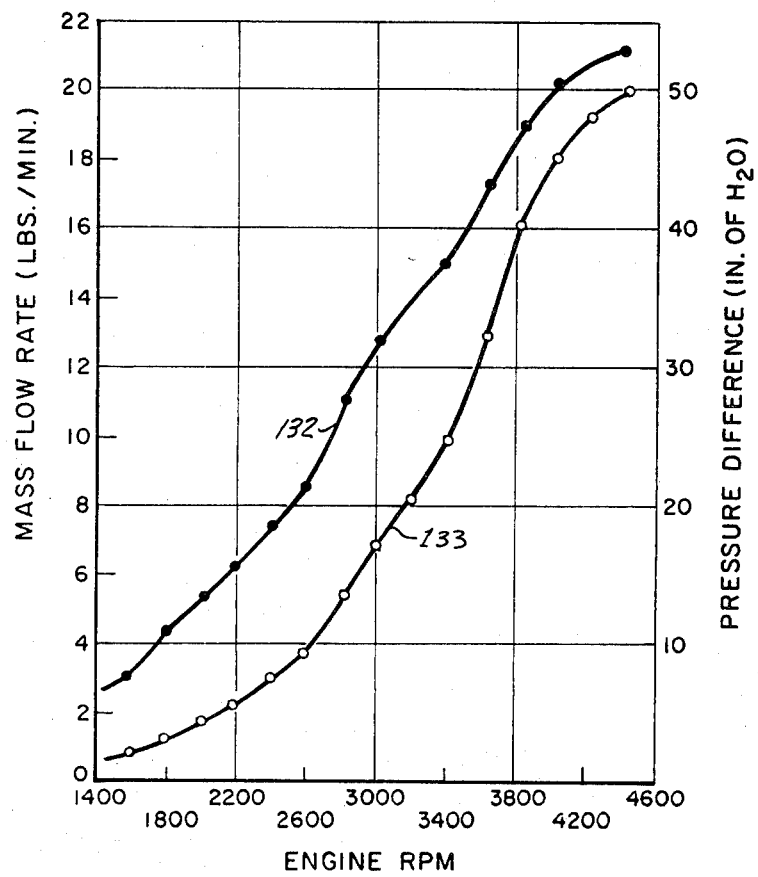

Another advantageous embodiment of vortex generator 11 is the embodiment of FIG. 9 of application Ser. No. 951,621, wherein hoses 120 and 121 are coupled by a T-connection to one input of ΔP transducer 14, and the length of rod 16 is extended into the bore as with the embodiment of FIG. 3 herein.

Figure 4A:
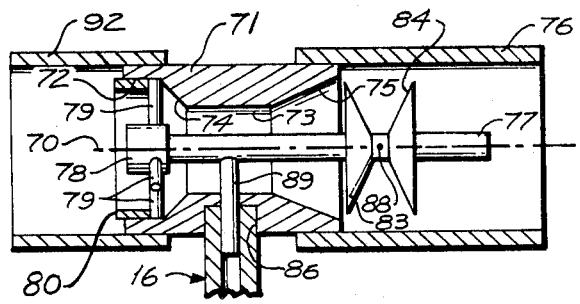
FIGS. 4A and 4B are a side sectional view and an end sectional view, respectively, of another embodiment of a flowmeter incorporating the principles of the invention.
Figure 4B:
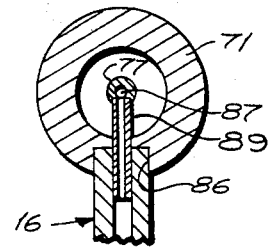

In FIGS. 4A and 4B is shown another preferred embodiment of vortex generator 11. In alignment with an axis 70, a nozzle body 71 has a flow passage from end to end comprising a cylindrical bore 72, a smaller cylindrical throat section 73, a converging conical section 74 connecting bore 72 to throat section 73, and a diverging conical section 75. Sections 73 through 75 comprise a converging-diverging nozzle with a cylindrical throat section. A cylindrical sleeve 76 fits over the downstream end of nozzle body 71 to enclose the space into which section 75 opens. A cylindrical sleeve 92 fits over the upstream end of nozzle body 71. Sleeves 76 and 92 have a larger cross-sectional area than the nozzle comprising sections 73 through 75. A cylindrical rod 77 is supported in alignment with axis 70 by a hub 78 attached to one end of rod 77 in bore 72 and a plurality (e.g., three) of spokes 79 attached to hub 78. Spokes 79 radiate from hub 78 to the surface of bore 72 where they are retained by an annular insert 80. Rod 77 extends from hub 78 completely through converging section 74, throat section 73, and diverging section 75, and through most of the interior of sleeve 76. Conical frustums 83 and 84 are mounted on rod 77 in alignment with axis 70 within sleeve 76. The bases of frustums 83 and 84 have flat circular surfaces, the bases of frustum 83 facing toward section 75 and the base of frustum 84 facing away from section 75. Frustums 83 and 84 are spaced from each other in apex to apex arrangement. Preferably, the base diameter of frustums 83 and 84 is a multiple of the spacing therebetween. Input conduit 16 fits in a counterbore 86 formed in the side of nozzle body 71. A passageway 87 extends through rod 77 from input conduit 16 to the space between frustums 83 and 84 where it opens into the interior of sleeve 76 through a plurality of holes 88, preferably four in number, spaced at 90° intervals. A connecting tube 89 couples input conduit 16 to passage 87.

The open end of sleeve 92 comprises a gas inlet, the open end of sleeve 76 comprises a gas outlet, bore 72, sections 74, 73, and 75, and the interior of sleeve 76 comprises a flow passage between the inlet and the outlet. Section 73 comprises a restriction. Frustums 83 and 84 together comprise a plurality of bluff bodies. ΔP transducer 14 senses the pressure at a point between the restriction and the bluff bodies, namely, where holes 88 are formed in rod 77 at the apexes of frustums 83 and 84 in the center of the annular channel formed therebetween. Here the vortices generated by the device are maximized. In addition to supporting rod 77 it is believed that hub 78 also increases the vorticity in the vortex generator.

Instead of the arrangement of bluff bodies shown in FIG. 4A, any of the arrangements of bluff bodies shown in my copending application Ser. No. 886,288, filed Mar. 13, 1978, the disclosure of which is incorporated fully herein by reference, could be employed.

In a typical example, the device of FIGS. 4A and 4B would have the following dimensions: inside diameter of insert 80 - 0.45 inch; length of insert 80 along axis 70 - 0.125 inch; base diameter section 74 - 0.5156 inch; length of section 74 parallel to axis 70 - 0.100 inch; half angle of section 74 - 45°; diameter of section 75 along axis 70 - 0.525 inch; half angle of section 75 - 20°1'; base diameter of frustums 83 and 84 - 0.500 inch; height of frustums 83 and 84 along axis 70 - 0.100 inch; half angle of frustums 83 and 84 - 63°27'; inside diameter of sleeves 76 and 92 - 0.625 inch; length of sleeve 76 from section 75 to the outlet - 0.750 inch; length of sleeve 92 from bore 72 to the inlet - 0.350 inch; distance from the end of rod 77 to the outlet - 0.200 inch; distance from the end of section 75 to the base of frustum 83 - 0.020 inch; spacing between the apexes of frustums 83 and 84 - 0.050 inch; distance from the base of frustum 84 to the end of rod 77 - 0.280 inch; inside diameter of passage 87 - 0.086 inch; inside diameter of tube 89 - 0.054 inch; diameter of holes 88 - 0.032 inch.

In each of the embodiments of FIGS. 3 and 4, a restriction and one or more bluff bodies are formed in the flow passage, and the difference in gas pressure is sensed between a point outside the flow passage in communication therewith and a point inside the flow passage between the restriction and the bluff body. This pressure difference has been found to be proportional to the square of the mass flow rate of the gas over a continuous range from an infinitesimally small flow rate upward, even though the gas is compressible. To accommodate larger flow rates without creating an excessive ΔP, the dimensions of the vortex generator or the cross-sectional area of the flow line when the vortex generator is connected as a bypass are simply scaled up in size. The sensed pressure difference may be viewed as a vacuum signal in that the pressure is less than the ambient pressure upstream or downstream of the vortex generator. Relative to the known prior art, surprisingly large pressure differentials, i.e., vacuum signals, are so generated, with an extremely small pressure drop across the transducer. Such vacuum signals can be accurately generated at flow velocities too low to be measurable by any conventional means.

In each of the embodiments of FIGS. 3 and 4, the flow passage, the restriction, the bluff bodies, and the outlet are aligned with a common flow axis, namely, axis 44 in FIG. 3 and axis 70 in FIG. 4, and the inlet to the flow passage is aligned with an inlet axis lying in the same plane as the flow axis. In FIG. 3, the inlet axis is transverse to and intersects the flow axis. In FIG. 4, the inlet axis is aligned with the flow axis.

It is well known that the aerodynamic drag resulting from a bluff body is related by a drag equation to a drag coefficient gas density, gas velocity, and wetted area, the four quantities that absolutely determine mass flow rate. The drag coefficient is related to geometric shape of the bluff body and Reynold's Number. It is believed that the vortex generators shown in FIGS. 3 and 4, and in the referenced patent and applications, totally convert the drag of the bluff body into stable and continuous, low pressure-producing vortices of the nature described in my copending application Ser. No. 886,289. Specifically, the bluff body generates the vortices and the annulus formed in the flow passage by the bluff body together with the restriction confines and forces the vortices to follow a continuous stable path rotating about the flow axis. The low pressure produced by the vortices gives rise to the measured pressure produced by the vortices gives rise to the measured pressure difference, i.e., the vacuum signal. Confirmation of this theory in relation to the drag equation is given by the following facts: (1) the measured pressure difference is proportional to the square of the mass flow rate, and, in the drag equation, drag is proportional to the square of the gas velocity; (2) when the Reynolds Number is below a threshold (1000 for discs), the drag coefficient becomes linearly related to Reynolds Number and velocity, and the ΔP is proportional to velocity; (3) the measured pressure difference is indicative of mass flow rate irrespective of gas compressibility, and drag is related by the drag equation to the four quantities that totally determine mass flow rate; (4) the vortex generated vacuum is linearly related to the pressure drop across the transducer; (5) the vacuum signal increases as the Reynolds Number decreases for a given flow rate because drag increases with decreasing Reynolds Number; and (6) in the higher Reynolds Numbers, the drag coefficient is constant and the flowmeter is unaffected by viscosity or Reynolds Number changes.

Figure 5:
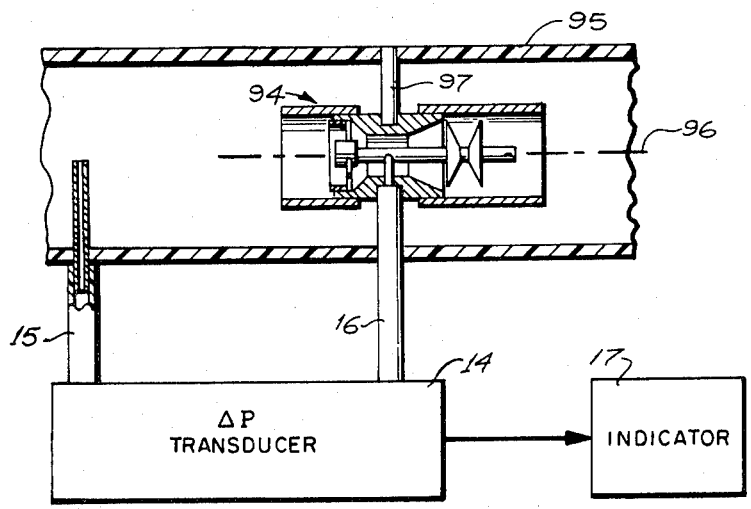
FIG. 5 is a side sectional view of the flowmeter of FIG. 4 in a fluid system.

In FIG. 5, the vortex generator of FIGS. 4A and 4B, designated 94, is supported inside a flow line 95 in alignment with its axis 96 by a rod 97, as well as input conduit 16 of ΔP transducer 14. Preferably, as shown in FIG. 15, input conduit 15 of ΔP transducer 14 protrudes into the interior of vortex generator 94 at a point A spaced upstream of the inlet insert designated 80 in FIG. 4A. It has been found that exposure of inlet conduit 15 to the pressure at point A provides a more accurate representation of vortex activity and a much stronger signal from ΔP transducer 14. It is believed that input conduit 15 so placed reads a local static pressure and that such reading reflects vortex vacuum activity at point B. Alternatively, however, input conduit 15 could be placed to protrude into the interior of flow line 95 at a point A' upstream of vortex generator 94 spaced therefrom, a distance that is preferably at least equal to the frustum diameter, and preferably equal to two to four frustrum diameters. Indicator 17 provides a reading of the pressure difference between the tap-in point A (or A') in communication with the upstream of vortex generator 94 and the tap-in point B inside vortex generator 94. Functionally, the arrangement of FIG. 5 is equivalent to that of FIG. 2 in that a major portion of the gas flowing through line 95 is bypassed through vortex generator 94. The bypassed portion is sensed, and the resulting pressure difference accurately represents the total mass flow rate of the gas passing through line 95.

Although sleeves 76 and 92 are desirable, they are not essential to the described operation of device 94. Sleeve 76 serves to further contain the vortices and thus increase the vacuum signal.

Figure 6:
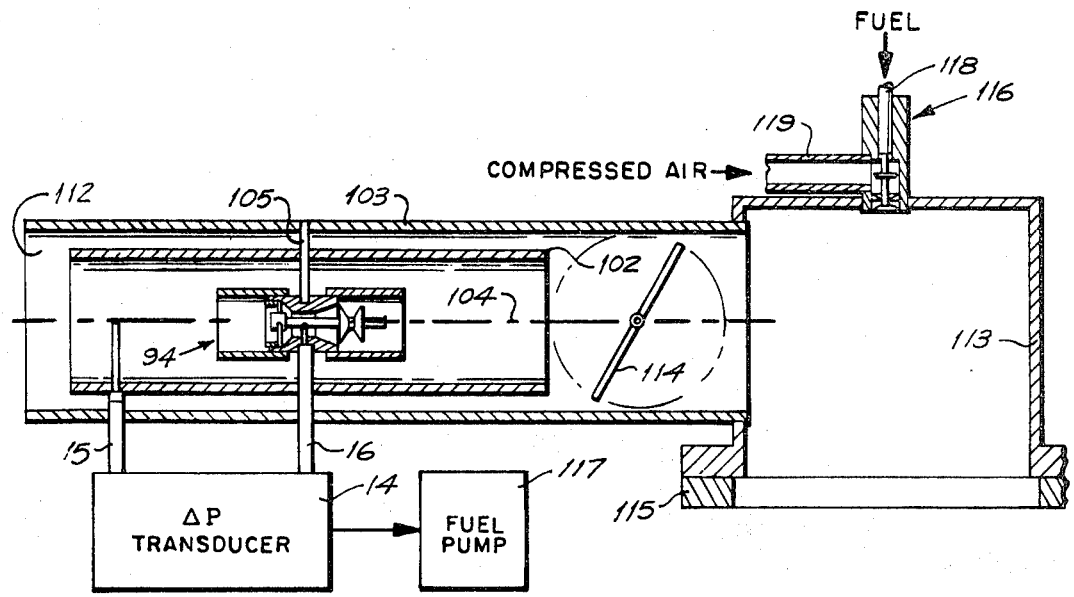
FIG. 6 is a side sectional view of the flowmeter of FIG. 4 surrounded by a sleeve in the intake system for fuel injection internal combustion engines.

In FIG. 6, the vortex generator of FIGS. 4A and 4B, designated 94, is located in a sleeve 102 in a gas line 103. In this embodiment, line 103 is the inlet air scoop of a fuel injection internal combustion engine. Vortex generator 94 and sleeve 102 are supported in alignment with an axis 104 of line 103 by a support rod 105, as well as input conduit 16 to a $\Delta P$ transducer 14. Input conduit 15 of $\Delta P$ transducer 14 opens into the interior of sleeve 102 upstream of vortex generator 94.

Air drawn into an inlet 112 by the engine vacuum flows through line 103 to an air-fuel mixing chamber 113. A butterfly valve 114, which is located downstream of sleeve 102 near the entrance to mixing chamber 113, is controlled by the throttle of the engine in conventional fashion. Mixing chamber 113 is secured to a mounting flange 115 of the engine intake manifold. Into the top of mixing chamber 113 is injected fuel by a nozzle 116, which is preferably the device shown in FIG. 1 of my copending application Ser. No. 951,621, modified so the rod extends into the restriction as shown in FIG. 2 thereof. A fuel pump 117 is connected by a fuel line 118 to the liquid inlet of nozzle 116, and an air compressor (not shown) is connected by a conduit 119 to the gas inlet of nozzle 116. The described arrangement forms in effect a double bypass in that vortex generator 101 samples only part of the gas flowing through sleeve 102, and sleeve 102 samples only part of the gas flowing through line 103.

$\Delta P$ transducer 14 is connected to fuel pump 117 to control the pressure thereof and thus change the quantity of fuel injected into mixing chamber 113 to correspond to changes in the air taken in through line 103, thereby maintaining an approximately constant air-fuel ratio under changing engine conditions. This embodiment illustrates that instead of reading out the vacuum signal produced by $\Delta P$ transducer 14, it could be employed for process control; in this case, control of the air-fuel ratio in the fuel injection internal combustion engine or to enhance any combustion process.

Figure 8:
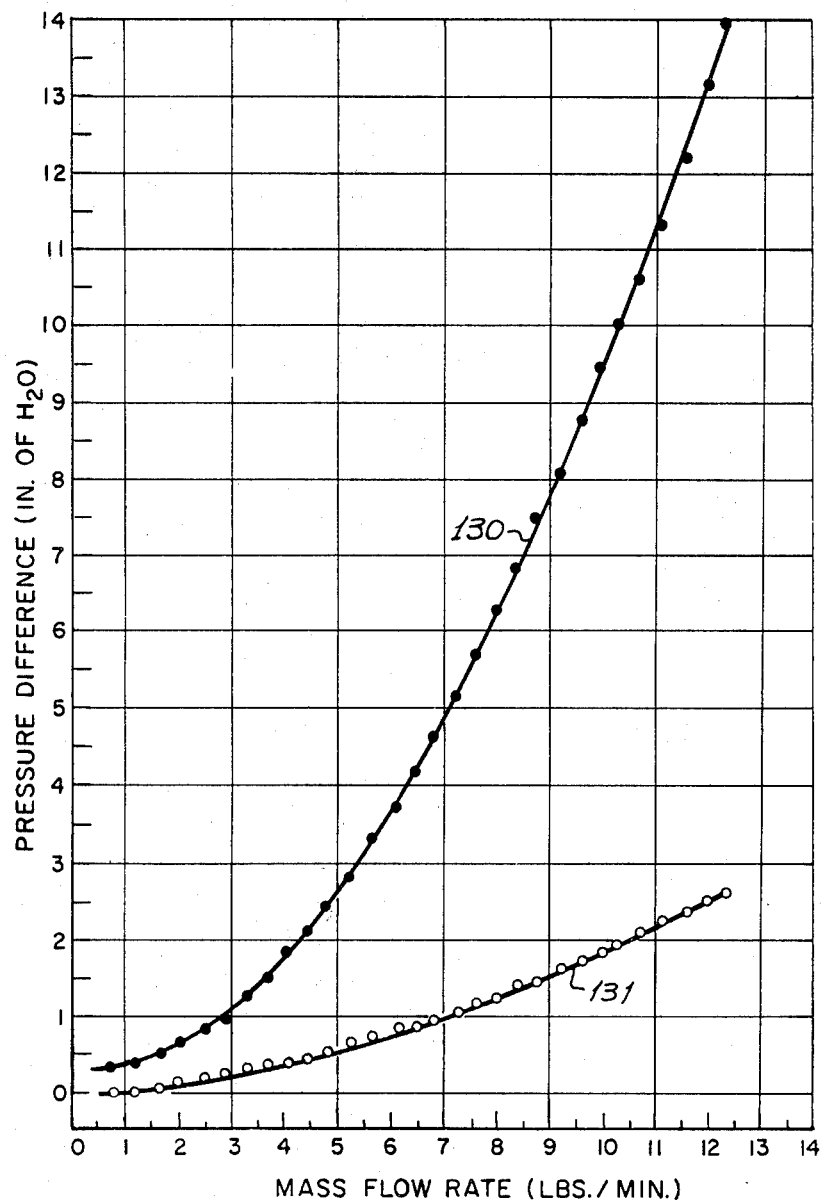
FIGS. 8 and 9 are graphs depicting flowmeter operation in the intake system of FIG. 6.

It is preferred to measure the pressure difference between the points, i.e., A and B, heretofore described. However, a useful repeatable measure of mass flow rate is also given by the sum of pressure at points A and B, alternatively at points A' and B. Tests were conducted in which the pressure sum was sensed. Actually two $\Delta P$ transducers were employed, one between Point A' and the gas source or plenum and another between Point B and the gas source, and the two transducer readings were added. In FIG. 8, a curve 130 represents the pressure sum in inches of water column of the readings measured by the two $\Delta P$ transducers as a function of the mass flow rate in lb/min entering inlet 112 in FIG. 6. Tests have shown that the response of the flowmeter, i.e., pressure sum as a function of mass flow rate, is totally repeatable and unaffected by ambient temperature and pressure. Thus, a direct reading of mass flow rate is provided without further computation or data processing despite the fact that the gas is compressible. If sleeve 102 were eliminated, the flowmeter would exhibit a similar response with a much larger vacuum signal, e.g., a pressure drop of approximately 20 inches of water column at approximately 8 lb/min. The response in both cases can be expressed by the following equation:

$$\dot{M} = -A\Sigma P^4 + B\Sigma P^3 - C\Sigma P^2 + D\Sigma P + E$$

where $\dot{M}$ is mass flow rate, A, B, C, D, and E are coefficients depending upon the dimensions of the components, and $\Delta P$ is the sum of the readings of the two $\Delta P$ transducers. In the system of FIG. 6 without sleeve 103, coefficient D is five orders of magnitude larger than coefficient A, three orders of magnitude larger than coefficient B, and one order of magnitude larger than coefficient C. Accordingly, the third and fourth orders of pressure difference are in all cases very small, and over relatively large ranges of mass flow rate the second order of pressure difference is quite small so that mass flow rate is approximately a linear function of pressure difference.

In FIG. 9, curve 132 represents the mass flow rate in pounds per minute entering inlet 112 in FIG. 6 as a function of engine RPM for varying horsepower loads, and curve 133 is the pressure difference in inches of water column measured by transducer 14 as a function of engine RPM for these different power loads. The close correlation between curves 132 and 133 demonstrates the eminent suitablity of flowmeter 94 to sense mass flow rate for the purpose of controlling the quantity of fuel injection. As the ambient and engine conditions, namely, temperature, pressure, and load, change the functional relationship between mass flow rate and engine RPM also changes, but the response of flowmeter 94 does not, for it provides a reliable signal to control the fuel injection so as to maintain a constant desired mass air-fuel ratio. Curve 131 represents pressure difference or drop in inches of water column from inlet to outlet of flowmeter 94 in FIG. 6 as a function of mass flow rate in pounds per minute. It should be noted that in all cases there results a very small pressure drop approximately linearly related to the pressure difference measured by $\Delta P$ transducer 14. In this connection it should be noted that in the vortex generator of FIGS. 4A and 4B a decrease in the pressure drop across the generator results and the signal produced by the $\Delta P$ transducer increases when the diameter of frustums 83 and 84 is reduced and/or moved closer to the outlet and the diameter of sleeve 76 is increased. Specifically, when the area of the outlet annulus defined by the outer diameter of frustums 83 and 84 and the inner diameter of sleeve 76 is approximately equal to or less than the area of annulus defined by throat section 73 and rod 77, the signal strength of the $\Delta P$ transducer is maximized.

It is important to the invention that two properly placed pressure probes are used to derive the pressure data. One probe should be within the flowmeter to measure the vortex generated therein. The other probe should be at the inlet of the flowmeter where vortex activity has also been observed in practice and where the local ambient pressure reflects the effects of vortex activities in the vicinity of the vortex generating device.

It is believed that the two probes cancel the compressibility effects, thereby producing a true highly accurate mass flow measurement. In a typical embodiment of the intake system of FIG. 6, for example, the probe connected to input 15 was spaced upstream of the inlet of flowmeter 94 by 1.55 inches, i.e., slightly more than three frustum diameters, and extended inwardly to approximately perpendicularly intersect axis 104. In general, the end of the probe connected to input 15 would not be spaced from axis 104 a distance more than the inlet radius of vortex generator 94 so it would lie within the flow stream passing through vortex generator 94.

Despite the reduction in gas velocity in the embodiments of FIGS. 5 and 6, vis-a-vis, an in-line flowmeter handling the same mass flow, a large pressure difference, i.e., vacuum signal, is produced. The flowmeter of the invention is, therefore, able to measure accurately and repeatably and with large signal the mass flow rate at very small gas velocities and Reynolds Number.

In terms of the theory outlined above concerning the direct conversion of drag to vortex pressure, it is believed that this is attributable to a substantive order of magnitude decrease in the Reynolds Number produced by the single bypass and double bypass, respectively, for a given mass flow rate and flowmeter size. Due to the larger cross-sectional flow area provided by the bypasses, the gas velocity decreases thereby decreasing the Reynolds Number. Experimental data shows that the drag of a disc is approximately and uniquely constant in a range of Reynolds Numbers from 1000 up to 10 million. This provides a totally stable basis for the direct conversion of drag into mass flow over an unusually large flow range, which is why the "disc-like" frustum is the preferred embodiment. Below 1000, the drag increases approximately linearly as a function of Reynolds Number. This rapid linear increase is believed to be a major reason for the large vacuum signal along with other peripheral vortex phenomena in the line. As the Reynolds Number decreases, the drag coefficient in the drag equation dramatically increases, thereby increasing drag and thus the vortex vacuum and pressure differences. If the Reynolds Number is reduced sufficiently, the drag coefficient becomes an approximately linear function of the Reynolds Number.

Figure 7A:
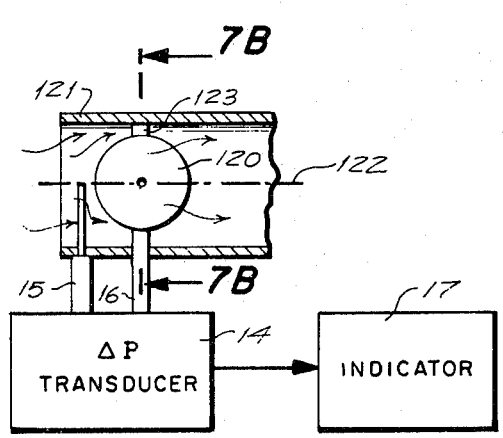
FIGS. 7A and 7B are side sectional and end sectional views, respectively, of another, simplified version of a flowmeter incorporating the principles of the invention.
Figure 7B:
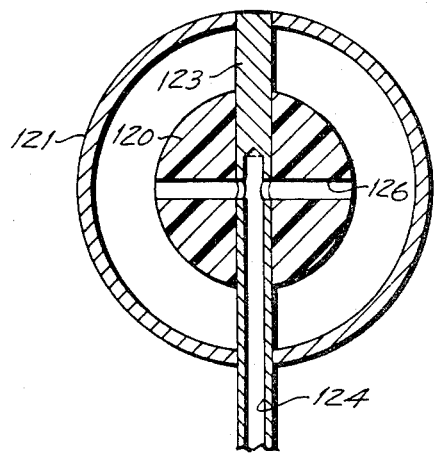

In FIGS. 7A and 7B, a spherical bluff body 120 is supported inside a gas line 121 in alignment with a central axis 122 by a rod 123 to form an annulus in the flow passage. Rod 123 passes completely through bluff body 120 perpendicular to axis 122 and is secured to line 121. Input conduit 16 of ΔP transducer 14 is formed by a passage 124 inside rod 123. A passage 126 extends from end to end through bluff body 120 perpendicular to rod 123 and axis 122, so as to interconnect with passage 124. Input conduit 15 opens into gas line 121 upstream of bluff body 120, preferably a distance at least equal to the diameter of bluff body 120. The leading half of the spherical surface of bluff body 120 effectively serves as a drag-producing bluff body, the surface thereof in the plane of the minimum cross section, i.e., in the plane of passage 126 and rod 123, serves as the restriction, and the pressure is effectively sensed between such bluff body and restriction, as in the other embodiments. Thus, ΔP transducer 14 produces a vacuum signal, i.e., a signal related to the difference between the ambient pressure in the unrestricted portion of line 121 and the pressure on the surface of bluff body 120 in the plane of the smallest cross section area in line 121. Although the vacuum signal in this embodiment is not as sensitive or as large in magnitude as a number of the other embodiments, it is satisfactory for some purposes, including the actuation of bistable devices. The device does not lend itself to the double bypass method of the other embodiments.

The described embodiments of the invention are only considered to be preferred and illustrative of the inventive concept; the scope of the invention is not to be restricted to such embodiments. Various and numerous other arrangements may be devised by one skilled in the art without departing from the spirit and scope of this invention. For example, instead of coupling the output of the ΔP transducer to an indicator as shown in each embodiment, it could be coupled to some other utilization device, such as a bistable or analog valve, for control purposes. Instead of using the flowmeter to measure mass flow rate, it could be used to measure temperature. Alternatively, the frequency of the vortices within the flowmeter could be sensed with a microphone and compared with the frequency outside the flowmeter.

What is claimed is:

1. A vortex generating flowmeter comprising:
   a first port;
   a second port;
   a flow measurement passage between the first and the second ports;
   a restriction formed in the flow passage between the first and second ports;
   bluff body means producing drag in the passage between the restriction and the second port; and
   means for sensing gas pressure in the vicinity of the bluff body means between the restriction and the second port.

2. The flowmeter of claim 1, in which the first port is an inlet and the second port is an outlet.

3. The flowmeter of claim 2, additionally comprising a gas line and means for connecting the gas line to the passage so as to induce flow through the passage from the inlet to the outlet.

4. The flowmeter of claim 2, in which the inlet, the outlet, and the passage are aligned with a common flow axis.

5. The flowmeter of claim 4, in which the restriction comprises a converging-diverging nozzle with a cylindrical throat section.

6. The flowmeter of claim 5, in which the portion of the passage between the restriction and the outlet is cylindrical and larger in cross-sectional area than the nozzle.

7. The flowmeter of claim 6, additionally comprising a rod on which the bluff body means is mounted, the rod being aligned with the common flow axis and extending through the restriction.

8. The flowmeter of claim 7, in which the bluff body means comprises first and second frustums in alignment with the common flow axis, the base of the first frustum facing the restriction, the first and second frustums being arranged vertex to vertex.

9. The flowmeter of claim 8, in which the first and second frustums are spaced from each other.

10. The flowmeter of claim 9, in which the rod is hollow and has one or more openings between the first and second frustums and the sensing means comprises a differential pressure transducer, one input of which communicates with the hollow rod to sense the pressure between the first and second frustums.

11. The flowmeter of claim 4, additionally comprising a sleeve surrounding the flow measurement passage to provide an annular flow passage bypassed by the flow measurement passage.

12. The flowmeter of claim 11, additionally comprising a gas line having a cross-sectional area larger than the sleeve and means for mounting the sleeve in the line to form a further annular passage bypassed by the first named annular passage.

13. The flowmeter of claim 12, in which the sensing means comprises a differential pressure transducer, one input of which communicates with the interior of the sleeve at a point outside the flow measurement passage.

14. The flowmeter of claim 13, in which the input of the differential pressure transducer communicates with the interior of the sleeve at a point spaced upstream from the inlet of the flow measurement passage.

15. The flowmeter of claim 2, additionally comprising a gas line and means for connecting the passage in line with the gas line.

16. The flowmeter of claim 2, additionally comprising a gas line and means for connecting the passage to bypass the gas line.

* * * * *